(12) United States Patent
Houle et al.

(10) Patent No.: US 7,803,113 B2
(45) Date of Patent: Sep. 28, 2010

(54) ULTRASOUND IMAGING OF ROTATION

(75) Inventors: Helene C. Houle, Sunnyvale, CA (US); Georg Schummers, Munich (DE); Bernhard Mumm, Mammendorf (DE); Christian Galuschky, Munich (DE); Marcus Schreckenberg, Freising (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 568 days.

(21) Appl. No.: 11/453,788

(22) Filed: Jun. 14, 2006

(65) Prior Publication Data

US 2008/0009734 A1 Jan. 10, 2008

(51) Int. Cl.
A61B 8/00 (2006.01)
(52) U.S. Cl. .................. 600/443; 600/438; 600/437
(58) Field of Classification Search ........... 600/437, 600/438, 441, 443
See application file for complete search history.

(56) References Cited

U.S. PATENT DOCUMENTS

| | | |
|---|---|---|
| 6,527,717 B1 | 3/2003 | Jackson et al. |
| 2004/0249273 A1 * | 12/2004 | Briandet et al. ............. 600/431 |
| 2005/0070798 A1 | 3/2005 | Pedrizzetti et al. |
| 2005/0074153 A1 | 4/2005 | Pedrizzetti et al. |
| 2005/0096543 A1 | 5/2005 | Jackson et al. |
| 2005/0107704 A1 | 5/2005 | Von Behren et al. |
| 2005/0203395 A1 | 9/2005 | Sui et al. |
| 2005/0288589 A1 | 12/2005 | Houle et al. |
| 2006/0004291 A1 * | 1/2006 | Heimdal et al. ............. 600/459 |
| 2006/0058618 A1 * | 3/2006 | Nishiura ..................... 600/407 |
| 2009/0099449 A1 * | 4/2009 | Lundberg ................... 600/443 |

OTHER PUBLICATIONS

"Strain and Strain Rate Parametric Imaging. A New Method for Post Processing to 3-/4-Dimensional Images from Three Standard Apical Planes. Preliminary Data on Feasibility, Artefact and Regional Dyssynergy Visualization," by Asbjørn Støylen et al.; Cardiovascular Ultrasound 2003 I:II; article available at http://www.cardiovascularultrasound.com/content/I/I/II; Published Aug. 25, 2003; 12 pages.

* cited by examiner

*Primary Examiner*—Brian Casler
*Assistant Examiner*—Amanda Lauritzan

(57) ABSTRACT

Rotations at multiple longitudinal levels (e.g., rotations from different short axis views) are determined. Three-dimensional representations are generated as a function of the rotations, such as distorting the representation to show rotation and/or modulating the display values as a function of the rotations. Twist and/or torsion of the heart may be calculated from the rotations.

10 Claims, 5 Drawing Sheets

| Speckle tracking of all views of the left ventricular endocardium, myocardium and/or the epicardium. |
|---|

| Use raw data to build dynamic left ventricular 4D model. Map rotation motion at appropriate levels on the 4D LV model. Auto level selection |
|---|

| Build dynamic Left ventricular bull's eye model: color (parameter) updates with each frame |
|---|

Figure 12

| Parametric Display on:<br><br>- Dynamic LV model<br>- Dynamic Bulls-eye | Graph Display of:<br><br>- Rotation for all segments<br>- Rotation Rate for all segments<br>- Global Twist<br>- Global Torsion | Parameter Extraction:<br><br>- Endocardial rotation for all segments<br>- Endocardial time to peak rotation<br>- Epicardial rotation for all segments<br>- Epicardial time to peak rotation<br>- Rotation gradient of endo and epi rotation<br>- Endocardial rotation rate for all segments<br>- Endocardial time to peak rotation rate<br>- Epicardial rotation rate for all segments<br>- Epicardial time to peak rotation rate<br>- Rotation rate gradient of endo and epi rotation rate<br>- Global Twist<br>- Time to peak twist<br>- Time to peak torsion<br>- % LV length 0 crossing of baseline and peak rotation |
|---|---|---|
| Type of Parametric Display:<br><br>- Color maps<br>- Vectors<br>- Point trajectory | | |
| Parametric Display of:<br><br>- Peak rotation<br>- Time to peak rotation<br>- Peak rotation rate<br>- Time to peak rotation rate<br>- Time to un-rotation<br>- Twist<br>- Torsion<br>- % LV length 0 crossing of baseline and peak rotation | | |

ULTRASOUND IMAGING OF ROTATION

BACKGROUND

This present description relates to medical ultrasound imaging. In particular, parametric imaging for rotational motion of the heart is provided with ultrasound imaging.

Ultrasound is used to assist in diagnosis of heart conditions. Doppler velocity and/or B-mode imaging of the heart provides real-time images of the heart. Two or three dimensional images are viewed as static images or dynamic clips. However, other analysis or characteristics may be derived from ultrasound information, such as strain or strain rate.

In "Strain And Strain Rate Parametric Imaging. A New Method For Post Processing Three Standard Apical Planes To 3-/4-Dimensional Images. Preliminary Data On Feasibility, Artefact And Regional Dyssynergy Visualization," Støylen et al. describe off-line visualization for heart diagnosis. In U.S. Application Publication No. 2005/0288589, parametric imaging of the heart is derived from ultrasound information. Dynamic clips or videos of the parametric imaging provide temporally useful information to a user. The parametric imaging may include values determined from data at different locations or different times, such as strain or tissue tracking values. The parametric values may be derived from heart cycle phase information. The ultrasound data may be responsive to contrast agents. The ultrasound data may be acquired with a three-dimensional scan or a plurality of two-dimensional scans.

Tissue tracking with ultrasound data may provide some rotational information. Data for a single, two-dimensional plane is acquired of a short axis view of the left ventricle of the heart. Tissue tracking with the data determines the circumferential motion. In magnetic resonance imaging, the torsion of the heart may be calculated. However, the torsion has insufficient temporal resolution for clinical utility.

BRIEF SUMMARY

By way of introduction, the preferred embodiments described below include methods, systems and computer readable media for representing and/or determining rotation information of a heart with ultrasound. Rotations at multiple longitudinal levels (e.g., rotations from different short axis views) are determined. Three-dimensional representations are generated as a function of the rotations, such as distorting the representation to show rotation and/or modulating the display values as a function of the rotations. Twist and/or torsion of the heart may be calculated from the rotations. Any one or combination of features disclosed herein may be used.

In a first aspect, a method is provided for representing rotation of a heart with ultrasound. First and second rotation components of the heart at first and second different longitudinal locations, respectively, of the heart are determined from ultrasound data. A three-dimensional representation is generated as a function of the first and second rotation components.

In a second aspect, a system is provided for representing rotation of a heart with ultrasound. A memory is operable to store ultrasound data representing different planes of the heart at different times. A processor is operable to determine, as a function of the ultrasound data, at least one rotation for each of the planes for each of at least two different times in a heart cycle, and operable to generate three-dimensional representations for each of the different times. Each three-dimensional representation is a function of the at least one rotation for each of the planes. A display is operable to display the three-dimensional representations in sequence.

In a third aspect, a computer readable storage medium has stored therein data representing instructions executable by a programmed processor for representing rotation of a heart with ultrasound. The storage medium includes instructions for determining rotation, twist, torsion or combinations thereof of the heart from ultrasound data, and displaying a three-dimensional representation of the rotation, twist, torsion or combinations thereof.

In a fourth aspect, a method is provided for determining rotation information of a heart with ultrasound. First and second rotation components of the heart at first and second different longitudinal locations, respectively, of the heart are determined from ultrasound data. A torsion, twist or torsion and twist are calculated as a function of the first and second rotation components.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In addition or alternative to strain or other parametric imaging of U.S. Application Publication No. 2005/0288589, rotation imaging or calculation is provided. The generation of parametric images, such as the generation of a dynamic surface, as disclosed in the above referenced application may be used for displays of rotation information. The above referenced application is incorporated herein.

The left ventricle of the heart moves in a complex pattern to pump blood into the body. A twist movement of the left ventricle may be modeled as a band. In the model, a muscle band is unwrapped in one piece. By wrapping around itself to form the heart wall, both ascending and descending portions result. Due to the structure and alignment of myocardial fibers, the left ventricle twists along the long axis, pulling down the base during systole. The amount of rotation, twist, or torsion may be an indicator of risk of heart failure. Normal twist may be about 7-10 degrees of the apex twisting relative to the base.

Ultrasound information is used to display or calculate twist of the heart or left ventricle. The twist component or amount of rotation motion is determined and displayed for different longitudinal locations. Ultrasound data is acquired from different planes or a volume including the different longitudinal locations. A surface representation may twist or the rotation may modulate the displayed color or brightness. A bull's-eye or polar mapping may represent twist. By combining motion components from different longitudinal locations in an image, the rotation, twist and torsion may be illustrated and/or calculated. Dynamic display or generation of representations as a function of time may further indicate changes in rotation, twist and torsion for one or more sectors of the heart.

Figure 1:
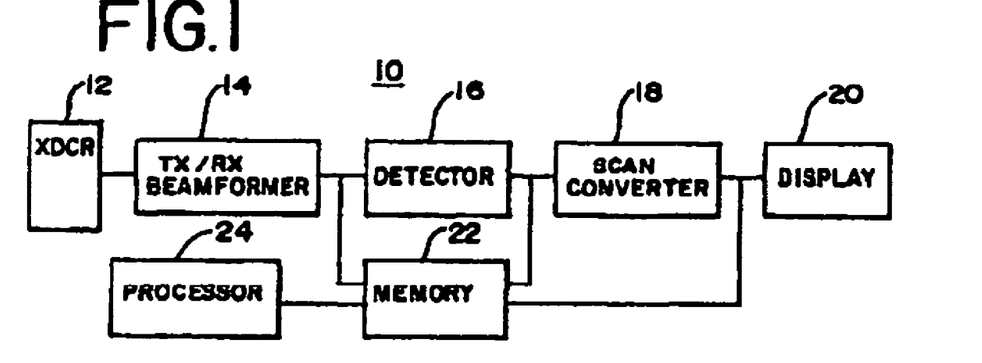
FIG. 1 is a block diagram of one embodiment of a diagnostic medical ultrasound imaging system for representing or calculating rotation information.

FIG. 1 shows a system 10 for representing rotation of a heart with ultrasound. The system 10 includes a transducer 12, a beamformer 14, a detector 16, a scan converter 18, a display 20, a memory 22, and a processor 24. Additional, different, or fewer components may be provided. For example, the processor 24 and memory 22 are provided on a separate system, such as a remote workstation or computer. The system 10 is a medical diagnostic ultrasound imaging system, such as a cart or portable system for real-time scanning of a patient. Post processes in an "off-line" mode or real-time processes may be provided on the system, allowing analysis of ultrasound data without transfer to remote systems. The imaging or calculation capability is located on a medical diagnostic ultrasound imaging system, but a separate computer, workstation or other system may be used.

The transducer 12 is a one, 1.25, 1.5, 1.75, 2 or other multi-dimensional probe. The transducer 12 is permanently or releasably connected with the system 10. Handheld, wobbler, catheter, endocavity, transesophageal (TEE) or other transducers 12 are used. In one embodiment, the transducer 12 is a single array, but multiple arrays of elements may be provided. The transducer 12 includes or does not include an absolute position sensor or other device for determining a current position or displacement associated with the transducer 12.

The beamformer 14 is a transmit, receive or both transmit and receive beamformer. As a transmit beamformer 14, a plurality of waveform generators or pulsers, delays, phase rotators, amplifiers, filters and/or other structures are provided in channels for generating relatively delayed and apodized electrical waveforms for the elements of the transmit aperture on the transducer 12. As a receive beamformer 14, a plurality of amplifiers, filters, delays, phase rotators, summers and/or other structures are provided in channels for summing relatively delayed and apodized receive signals. A single summer may alternatively be provided. The beamformer 14 includes a transmit and receive switch for selecting between transmit and receive paths or operation.

The beamformer 14 is operable to form ultrasound data along at least two different planes as a function of scanning. For example, at least two different planes are scanned by moving the transducer 12 to a new orientation or changing a scanning parameter to obtain a different plane with the transducer 12 in a same orientation or position. By applying different delay and apodization profiles, acoustic energy is generated to scan along different scan lines. Echo signals are delayed, apodized, and summed to form ultrasound data representing tissue, fluid or other structure along the scan lines. A complete scan of a region generates a frame of data for a given time. For flow or Doppler processing, the frame of data for a given time may be associated with multiple transmissions. Given the speed of sound in tissue, the region is scanned at a substantially same time for a frame of data. More rapid scanning is provided in alternative embodiments by multiple beam transmission or reception or by plane wave transmission. By repeating the scan at different times, multiple frames of data for a same region at different times are provided.

Different planes are scanned by repositioning the transducer 12, a transmit aperture, a receive aperture or a scan plane position. Multiple planes are also scanned by electronically and/or mechanically scanning a volume, such as scanning with a wobbler array.

Any organ or tissue may be imaged. In one embodiment used as an example herein, different planes of the heart are scanned. For example, the user manually positions the transducer 12 to acquire ultrasound data from apical 4 chamber (A4C), apical 2 chamber (A2C) and apical long axis (ALA) scans of the heart. In another example, the transducer 12 acquires ultrasound data from three or more short axis views of the left ventricle, such as at the base (e.g., by the mitral valve), at a mid-papillary level, and at the apex (e.g., apical view with the transducer 12 angled such that the central cavity is almost gone from the view or as low down on the left ventricle as possible). Additional, fewer or different standard or non-standard views may be used, such as acquiring another short axis view between the papillary and apex or basal views.

Each of the scans is repeated at different times throughout at least a portion of one or more heart cycles. Scanning throughout one or more heart cycles may be used to increase an amount of data acquired for analysis. In one embodiment, data for a same view or scan plane acquired over different heart cycles is combined temporally to provide ultrasound data representing a single heart cycle. The ultrasound data for one or more cycles or portions of cycles is time warped to temporally align the data for combination. Alternatively, the acquisition of ultrasound data over multiple heartbeats is used to show changes from one heartbeat to the next or for oversampling and averaging to reduce artifact and noise within the data sets. The heart cycle timing relative to acquisition is derived from the ultrasound data or obtained from an ECG monitor input.

In one embodiment, a position sensor records the relative position of the acquisition planes. To know the position of a contour, plane or tissue, freehand acquisition uses position sensors. Using a rotational device, the image acquisition may be automated with known positions of scan planes relative to each other. The user positions the transducer 12 on a defined view (reference view), and the system 10 then acquires other views automatically. Scanning a volume electronically alternatively provides position information. The position information is later used for relative alignment of data from the different planes. Alternatively, an alignment is assumed, such as where standard views are used. In yet another embodiment, a TEE transducer 12 with a fixed rotational axis is used to acquire the ultrasound data. The later derived surface may be based on the endocardial surface or on the endocardial contours from multiple 2D planes.

The detector 16 is an intensity (e.g., B-mode or M-mode), velocity (e.g., Doppler velocity), Doppler tissue velocity, contrast agent (e.g., phase inversion), harmonic (e.g., receiving at a second harmonic of a transmitted frequency), or other now known or later developed detector or combinations thereof. The ultrasound data input is detected by the detector 16. In one embodiment, the detector 16 outputs velocity estimates for each spatial location or a subset of spatial locations within a scanned plane. In other embodiments, an intensity is output for each spatial location or for a selected line or curved line within a scanned plane. Similarly, contrast agent data based on Doppler or intensity processes may be output. The detector 16 outputs detected ultrasound data to the scan converter 18. The processor 24 may operate on or use the ultrasound data prior to or after scan conversion.

The scan converter 18 converts the ultrasound data from a polar coordinate or acquisition coordinate format to a Cartesian or display coordinate format. The scan converted ultrasound data is provided to the display 20 or the memory 22.

The display 20 is a CRT, LCD, projector, plasma screen, touch screen or other now known or later developed display device. Any types of images may be displayed, such as B-mode, M-mode, Velocity, or combinations thereof. The display 20 displays a three-dimensional representation as a parametric surface generated from the ultrasound data. The display 20 dynamically displays three-dimensional representations in sequence. A value (e.g., twist or torsion) may also or alternatively be displayed.

The memory 22 is a CINE memory, RAM, flash, hard disc, CD, DVD, removable media, cache, buffer, system memory or other now known or later developed memory for storing one or more frames of ultrasound data. In one embodiment, the memory 22 stores clips or a plurality of frames of data for each of the different scanned planes or for a scanned volume. Ultrasound data representing different planes and different times is stored, such as storing ultrasound data for at least three short axis planes spaced apart along a longitudinal axis of the heart and for one or more longitudinal views. The memory 22 acquires the ultrasound data from one or more different locations along the ultrasound data path between the beamformer 14 and the display 20.

The processor 24 is a control processor, central processing unit, general processor, application specific integrated circuit, field programmable gate array, digital signal processor, graphics processing unit, analog circuit, digital circuit, combinations thereof or other now known or later developed device for determining rotation components, calculating twist, calculating torsion, and/or generating a three-dimensional representation. The processor 24 is a single device or a network or grouping of a plurality of devices. For grouping a plurality of devices, the devices operate sequentially and/or in parallel.

The processor 24 is operable to determine a rotation or rotation component as a function of the ultrasound data. A rotation component is the rotation amplitude, rotation phase relative to the heart cycle, rotation vector (e.g., 1D, 2D or 3D) or other component of rotation. For short axis viewing planes of the heart, the rotation is a circumferential displacement for the heart wall or tissue. Rotation about an axis or point, even for movement along a line, may be determined. The heart wall or tissue may displace between scans. For short axis views, the tissue for the cross-section of the heart chamber may rotate about a center, longitudinal axis or other point in the plane. For long axis views, the tissue for the cross-section of the heart chamber may rotate about a point in the chamber, a center of the chamber, or other location determined automatically or manually.

Tissue or speckle tracking with B-mode information is used to determine the displacement or rotation of the tissue between the scans or data acquired at different times. For example, displacement is determined by correlation of intensity speckle, features or tissue between frames of data acquired at different times. In one embodiment, speckle or other tracking disclosed in U.S. Application Publication Nos. 2005/0070798 and/or 2005/0074153, the disclosures of which are incorporated herein by reference, is used. A Fourier analysis may be used to determine displacement. In another example, velocity is determined using Doppler estimation techniques, analysis of D-mode data, or combinations thereof, such as described in U.S. Pat. No. 6,527,717, the disclosure of which is incorporated herein by reference. The velocity tangential to the tissue is used as the rotation component.

Another rotation component may be calculated from the rotation. For example, the relative phasing as compared to the heart cycle of the rotation is determined as a motion component. The phase or amplitude parameter disclosed in U.S. Application Publication No. 2005/0107704 and 2005/0203395, the disclosures of which are incorporated herein by reference, may be used. In one embodiment, the starting point is the R-wave as a non-rotated position. The timing of a threshold amount of rotation relative to the entire heart cycle (e.g., at half or 50%, earlier or later) is calculated and used as the rotation component. The timing relative to the heart cycle is of a zero-crossing or halfway point of total rotation, or of a change of direction of rotation.

Figure 9:
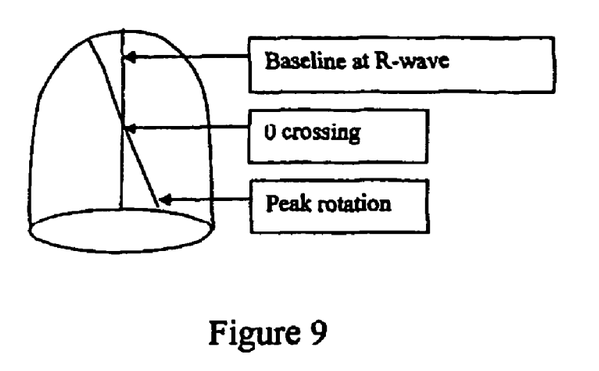
FIG. 9 is a graphical representation of a display of rotation information in one embodiment.

Other relative timings of rotation to a heart cycle may be used. For example, FIG. 9 shows a % or longitudinal location along the left ventricular length of a 0 crossing of baseline and peak rotations. The vertical line represents no or little rotation, such as at diastole or the R-wave. A peak rotation or twist is determined over at least one heart cycle, such as associated with peak systole. The heart rotates during the heart cycle, so the vertical lines shifts. For example, the base line at the apex shifts left and at the base shifts right. Where the base and peak rotation lines intersect identifies a longitudinal location. The longitudinal location may be converted to a percentage of the left ventricular length where the apex is 0% and the base is 100%. The percentage or longitudinal location of the zero crossing of the peak rotation may indicate healthy operation of the heart or a disease state.

The rotation components are determined from ultrasound data at different locations, different times or both the different locations and different times. For example, rotations are determined from ultrasound data representing different spatial locations in a same frame of data or plane. Different segments or portions of the heart tissue at a given short axis, long axis or other view may rotate by different amounts due to compression or expansion of the tissue (e.g., strain). In one embodiment, the heart or left ventricle is divided into any number of segments. In other embodiments, each or a plurality of cross-sections of the heart tissue is divided into any number of locations for separate rotation determination. For example, rotations are determined from the ultrasound data associated with heart tissue from each of the views, such as the three or more short axis views and/or one or more long axis views. For each view, the rotation is determined for each spatial location or for spatial locations (e.g., regions) of interest. Where two or more views intersect, the rotation in three-dimensions may be determined. Alternatively, an average or global rotation is determined for each view.

In one embodiment, color M-mode data, B-mode or other data associated with curved lines corresponding to the heart tissue for each of the planes is acquired. The curved lines correspond to the heart wall or tissue. The ultrasound data is formatted as a frames of data for two-dimensional regions or as a set of values along the curved line as a function of time (color M-mode). The curved lines or regions of interest are identified automatically or manually.

The processor 24 determines the contours from the views and determines rotation components for the spatial locations or segments along the curved lines 38. The ultrasound data for tissue tracking is acquired along the curved lines or within regions including the curved lines. By scanning the different views of the heart, two dimensional (2D) coordinates and rotation information of a contour 38 (see FIG. 3) representing a curved M-Mode 40 (see FIG. 4) positioned on the myocardium are acquired. For example, two or more longitudinal views (e.g., 2 chamber, 3 chamber and 4 chamber views) and two or more short axis views are acquired. The curved lines 38 may be determined from other types of ultrasound data.

The rotation components are determined for different times. Ultrasound data acquired at two or more different times is used to determine a rotation component. Rotation components associated with different times may be determined. Ultrasound data from a same time may be used in more than one determination of rotation components where ultrasound data from different times is also used. Recursive or non-recursive combination of the ultrasound data may be used. The processor 24 determines rotations for different times in the heart cycle for dynamic analysis or viewing of representations changing as a function of time.

The location of tissue being tracked may change over time. The curved lines 38 or regions of interest are tracked through multiple images. The tracking occurs automatically, such as using thresholds, speckle or tissue tracking or automated border detection. Alternatively, the user manually indicates a position of the region of interest or curved line 38 for each frame of data. Based on the regions of interest or curved lines 38 identified for different times, rotation components are determined. Alternatively, the processor 24 generates a dynamic 3D surface model in another format or using other techniques for determining rotation.

The processor 24, using a graphics card, the scan converter 18, a frame buffer, combination thereof or without other components, generates a three-dimensional representation, such as a parametric surface, as a function of the rotation components. The display 20 is operable to receive and display the three-dimensional representation. The three-dimensional representation represents a three-dimensional portion of the scanned tissue, such as the heart. The representation or surface values (e.g., color, brightness, and gray-scale) of the rotation components mapped to the surface graphically provide rotation information to the user. For dynamic display, three-dimensional representations are generated for different times. Each three-dimensional representation is a function of one or more rotations for one or more planes or scan locations.

Figure 5:
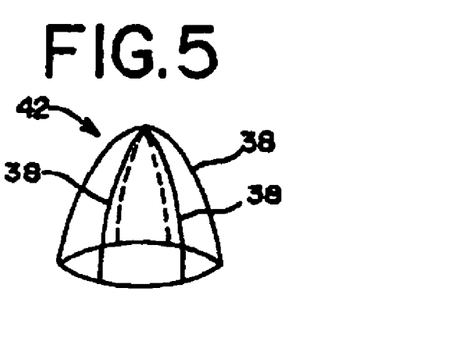
FIG. 5 is a graphical representation of one embodiment of a three dimensional representation of a surface.

In one embodiment shown in FIG. 5, the three-dimensional representation is a surface 42 representing the heart. For example, the surface 42 is of a portion of the heart, such as the left ventricle from a base to an apex portion. The curved lines 38 (see FIG. 3) are positioned relative to each other. In FIG. 5, three such curved lines 38 from A4C, A2C and ALA views are shown with about 60 degree spacing between each curved line 38. Approximated, estimated or actual relative positioning may be used, such as 30, 30, 120 degree spacing. The curved lines 38 are positioned based on expected or known relationship, such as using the three standard views of the heart, based on position sensing of the transducer 12, or based on assumption. The shape or contours formed by the relative placement of the curved lines 38 generally represents a shape of the heart or other structure at a given time. A Beutal three-dimensional representation of the heart or a portion of the heart is formed.

Rotation components may be determined for spatial positions along each of the curved lines 38. The curved lines 38 shown in FIG. 5 represent longitudinal views. Curved lines 38 may additionally or alternatively be provided for short axis views. The rotation components for latitudinal and/or longitudinal rotation are mapped to the surface 42. Parameters other than rotation components, such as wall thickness at a given time, strain, strain rate, velocity or in-plane displacement, may alternatively or additionally be mapped to the surface 42. Gray scale, color or both gray scale and color mapping are used. Texture mapping, look-up table or other mapping is used. The resolution of the mapping is binary or more complex. For example, rotation is separated into two or more ranges. Each range is displayed with a different color or shade.

For spatial locations on the surface 42 for which data is not available or acquired, such as between the curved lines 38, the rotation components are interpolated. Spherical interpolation is used, but other interpolation or extrapolation may be used. Applying a heart model based on standard views, the three dimensional (3D) surface 42 is reconstructed using interpolation. Data at a similar longitude, latitude, nearest neighbors or other motion parameter values are selected for weighted interpolation to a given spatial location on the three dimensional surface defined by the curved lines 38. Interpolation generates motion parameter values for some or most of the surface 42. Alternatively, a nearest or segment based rotation is mapped to a segment or region.

Figure 7:
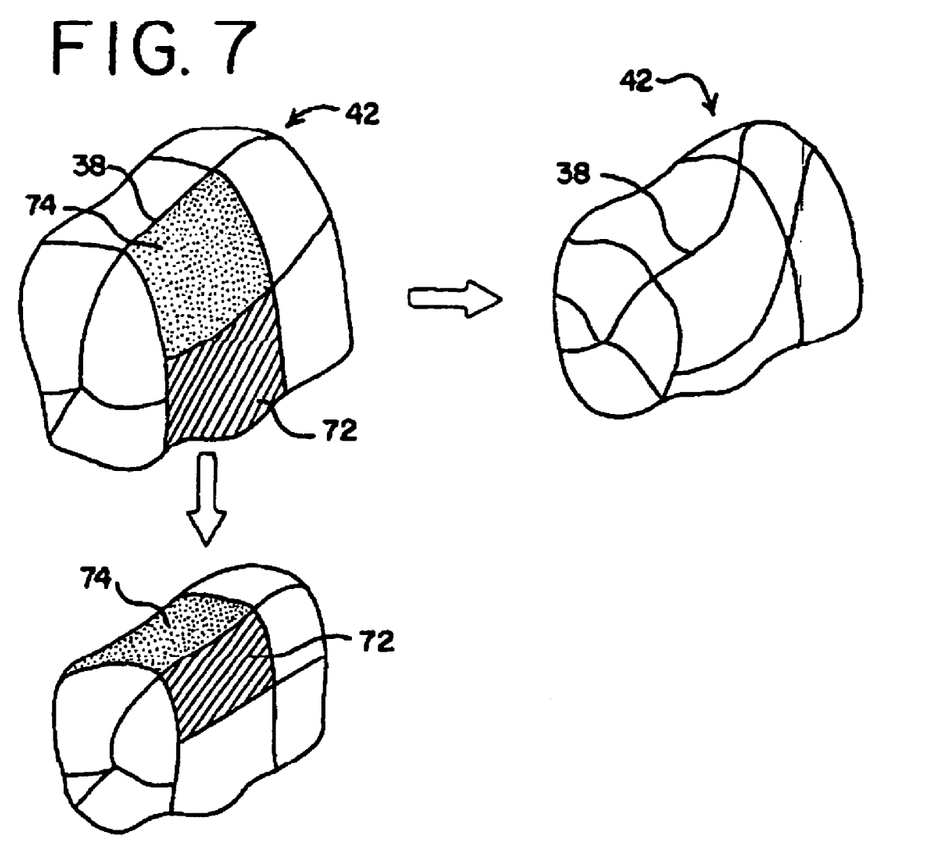
FIG. 7 is graphical representation of a three-dimensional surface showing rotation as a function of time.

With either point or region based mapping, different sections of the surface 42 are displayed as a function of corresponding rotation. FIG. 7 shows texture representing rotation components at sections 72 and 74. The sections or texture may shift, indicating rotation. The texture shift either shows movement of the same tissue due to rotation or shows the amount of rotation currently at a given location or section. The contour lines 38 may or may not be displayed.

In an alternative or additional embodiment shown in FIG. 7, the curved lines 38 deform as a function of the rotation components. Greater rotation components cause greater displacement of the lines 38. The points of intersection of the lines 38 may be displaced in three-dimensions as a function of rotation. Curve fitting is performed to connect the lines 38 from adjacent intersections. The amount of distortion represents the amount of rotation at a given time. Other points than at intersections may be used to distort the line 38. Two- or one-dimensional rotation components may be used.

In another alternative or additional embodiment, arrows or other graphics indicate rotation. The size, length or other characteristic of the graphic on the three-dimensional representation may indicate the magnitude or other characteristic of the rotation.

Figure 6:
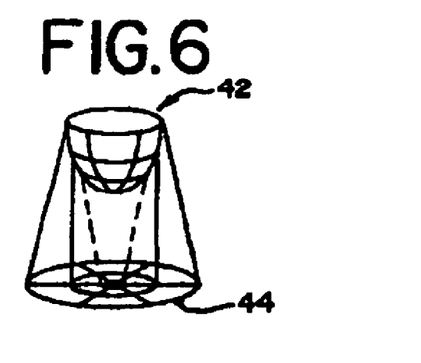
FIG. 6 is a graphical representation of one embodiment of derivation of and the resulting polar plot parametric surface.

In another three-dimensional representation, a polar plot 44 is generated as shown in FIG. 6. The contours or three-dimensional surface 42 formed by the curved lines 38 are projected onto a two-dimensional surface as the polar plot 44. FIG. 6 shows the projection of the portion of the heart where an apex is mapped to the center of the polar plot 44. The plot 44 includes a plurality of tissue regions, but may alternatively be free of contour lines. In other embodiments, the three-dimensional surface 42 is projected at other angles onto the polar plot 44. The rotation components or mapped display values (e.g., color or gray scale) are projected onto the polar plot 44. Interpolation is performed prior to or after projection. The polar plot 44 provides a two-dimensional parametric surface representing the three-dimensional structure of interest, such as the heart. Distortion of the lines and/or mapping of values onto the plot 44 indicates the rotation. Each of the heart tissue regions or points is displayed as a function of corresponding rotation.

Figure 8:
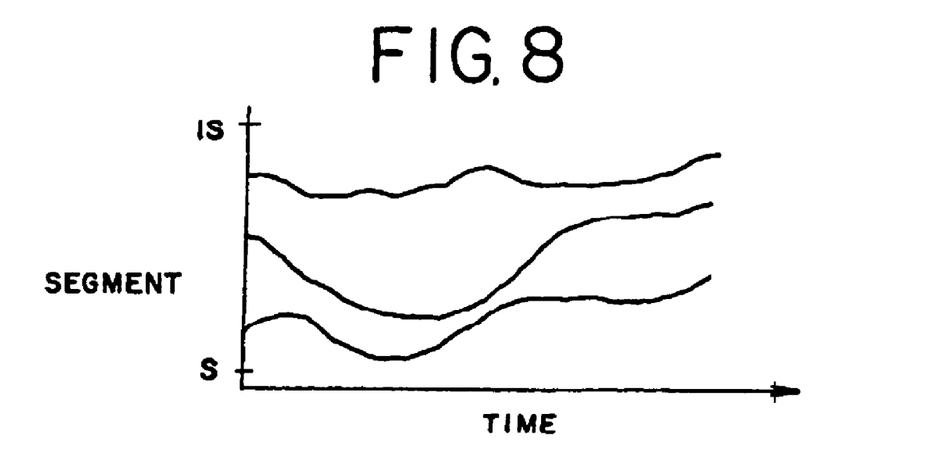
FIG. 8 is a graph representing rotation for different segments as a function of time.

Other three-dimensional representations may be generated. FIG. 8 shows a graph of segment rotation as a function of time. The time extends over one heart cycle, but may be longer or shorter. The difference from a resting or starting state is displayed along the vertical axis. Rotation for three segments is shown, but a greater or less number of segments may be shown. Where segments are associated with particular locations on the heart, the graph indicates rotation of the three-dimensional surface.

The three-dimensional representation is used to assess tissue function, such as systolic and diastolic function of the heart. The three dimensional representation of the parametric surface 42 provides a 3D model of the heart which enables a global visualization of rotation, twist and/or torsion of the heart.

To assist in visualization, the three-dimensional representation is displayed dynamically. The data representing the curved lines 38 at different times is arranged in sequence. After interpolation for each given time within the sequence, the three-dimensional representation is displayed dynamically. To simplify interpolation, a fixed relative transformation or relationship between the curved lines 38 over-time is assumed. Alternatively, the position of the curved lines 38 relative to each other varies as a function of time. The interpolation accounts for the variation. For a parametric surface of the heart, cardiac function is visualized during a portion or an entire heart cycle. For example, the dynamic parametric surface 42, 44 has colors that represent some aspect of the rotation of the myocardium (cardiac muscle). The colors change as a function of time, showing how the rotation components change with time. Alternatively or additionally, the tracked tissue is labeled differently. As the labels shift as a function of time, rotational motion is visualized.

The colors are shown on a moving surface, or shell. As the shape or other characteristic of the curved lines 38 changes, the shape of the surface 42, 44 changes. The moving surface represents the relative shape of the myocardium in general, or its endocardial surface in particular, throughout the cardiac cycle. In an alternative embodiment, the colors are shown on a static surface 42, 44 with only the colors or other display values changing as a function of time.

Additional indications may be added to the parametric surfaces 42, 44. For example, one type of motion parameter controls one characteristic of the display values (e.g., brightness or gray scale) and the rotation components control a different characteristic of the display values (e.g., color). As another example, landmarks, such as LVOT, MV, AV, ANTERIOR WALL, SEPTUM, and/or RV, for visualization help for better understanding of the orientation of a 3D surface model are added as annotations to the parametric surface 42, 44.

Where a user desires objective information, specific values may be displayed. For example, a localized region on the parametric surface 42, 44 is identified automatically or by the user. In one embodiment, the user positions a curved line different than the one used to form the parametric surface. An M-mode image, waveform or quantitative values are derived and displayed from the data of the parametric surface 42, 44. For example, peak velocity, time to peak velocity, A-wave velocity, mean strain, maximum strain or other now known or later developed quantitative values are calculated. As another example, rotation magnitude, rotation direction, heart cycle phase, regional time-to-peak or maximum twist, mean apical twist, median rotation, mean rotation, long axis shortening, mean apical, mid or basal rotation, time-to-peak apical, mid, or basal rotation, peak positive untwist rate and/or average rotation for a given plane or view are calculated for the line. For example, peak rotation is calculated, such as where negative values represent clockwise rotation and positive values represent counterclockwise rotation of the apex relative to the base. The values may be determined for the entire structure or specific locations.

In one embodiment, the processor 24 calculates twist. The difference in rotation of the apex relative to the base provides the twist. The direction of twist may also be provided, such as the apex rotation subtracted from the base rotation. The twist varies as a function of time. Alternatively, a mean apical twist is subtracted from a mean basal twist to determine a twist value for a heart cycle. A mean twist may also be calculated.

In an alternative or additional embodiment, the processor 24 calculates torsion. Torsion is the twist divided by the longitudinal or ventricular length. Since the length may vary during the heart cycle, the length is tracked. The distance from a center of the base to the apex defined by the contours 38 provides the length. As the contours 38 vary throughout the heart cycle, the length is determined. The torsion may vary as a function of time. Torsion is calculated for any given time or over time, and/or peak torsion over time is determined. Averages may be used to determine torsion for a heart cycle.

Figure 2:
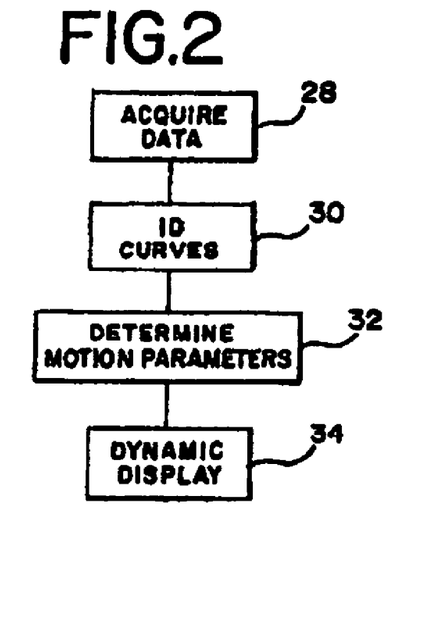
FIG. 2 is a flow chart of one embodiment of a method for representing rotation information.

FIG. 2 shows a method for representing rotation of a heart with ultrasound. Additional, different or fewer acts may be provided, such as performing acts 28, 30 and 32 without act 34. In another embodiment, an alternative or additional act to act 34 determines rotation information without or with display. The acts are performed in the order shown or a different order. The system 10 or a different system implements the acts.

Figure 3:
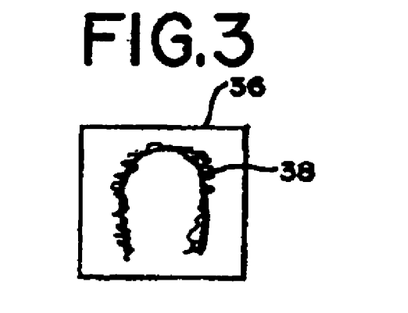
FIG. 3 is a graphical representation of a two dimensional scan of a heart.

In act 28, ultrasound data is acquired. The ultrasound data represents a desired tissue or structure, such as representing the heart. The ultrasound data corresponds to different positions within a volume, such as acquiring ultrasound data along at least two different planes. For the heart, the data is acquired from A4C, A2C and ALA views. FIG. 3 shows a two-dimensional scan of one view of the heart. Other views may be used, such as also acquiring data along two or more (e.g., 3 or 4) short axis views or other views corresponding to different longitudinal locations within the heart. The data is acquired by scanning along different planes or positions using two or three dimensional (volume) scans. Any now known or later developed type of data, such as intensity, Doppler tissue, velocity, contrast agent or combinations thereof may be used.

Figure 10:
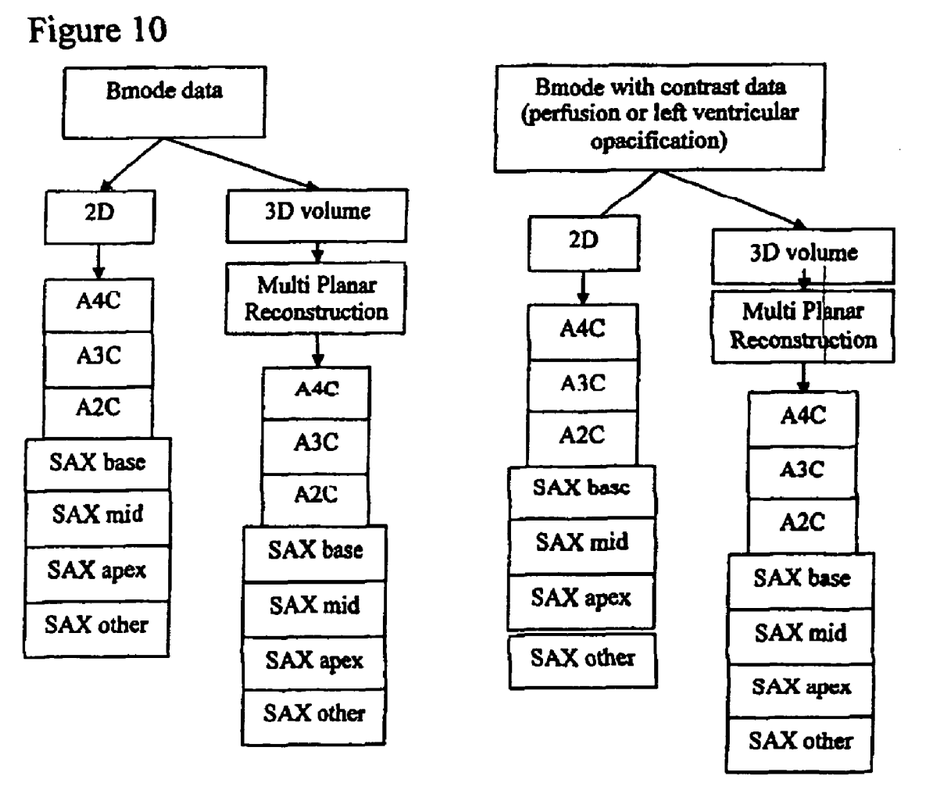
FIG. 10 is a graphical representation of input data in one embodiment.

FIG. 10 shows input data representing three apical views and four short axis views, but fewer, different or more views may be used. The apical views are A2C, A3C and A4C. The short axis views are apex, base, mid and one or more optional views. The data for the views are acquired from B-mode imaging or contrast agent imaging (e.g., B-mode based perfusion or opacification imaging). The data is acquired using two-dimensional scanning or from multi-planar reconstruction from volume scans. Other data sets, views, types of data, and/or types of scanning may be used.

Figure 4:
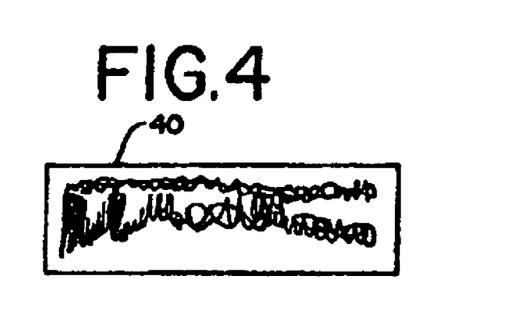
FIG. 4 is a graphical representation of a M-mode display in one embodiment.

The ultrasound data is acquired at different times. Different planes are scanned at the same or different times. For each plane or region, multiple scans are performed, such as scanning for at least a portion of or the entire heart cycle. FIG. 4 shows a curved M-mode scan 40 representing data acquired along the curved line 38 of FIG. 3 over multiple heart cycles. The acquired ultrasound data represents different spatial perspectives of the same region over a similar or same period of time. For example, scans of the heart in each of three or more different views are acquired at different times. Ultrasound data representing the corresponding region is acquired over a same portion or the entire heart cycle for each of the views.

In act 30, a curved line 38, such as within the planes 36 of the different 2D views, is identified for each of the scanned regions, such as within the planes of the different 2D views. In the example of FIG. 3, the curved line 36 identifies the ultrasound data associated with heart wall tissue. Curved lines 38 identifying related tissue are identified for the other views.

The curved lines 38 are identified manually through tracing or computer assisted manual tracing (i.e. identifying the curved line 38 after the user indicates the location of one or more landmarks). Alternatively, the curved lines 38 are identified automatically by applying an algorithm. The curved lines 38 are thin, such as one pixel wide, or thicker, such as 5 mm or other thickness wide.

The curved lines 38 are identified in one frame of data and then tracked to other frames of data. For example, velocity information is used to track movement of different portions of the curved line 38 throughout a sequence, such as disclosed in U.S. Application Publication No. 2005/0096543. As another example, speckle or tissue tracking with correlation, minimum sum of absolute differences or other function tracks the position of the curved lines 38 through a sequence, such as the tracking disclosed in U.S. Application Publication Nos. 2005/0070798 and/or 2005/0074153. Alternatively, manual tracing or automatic identification of each curved line 38 within a sequence is used independent of the curved lines 38 identified for other frames of data within the sequence.

By identifying the curved lines 38 throughout a sequence, ultrasound data associated with the tissue of interest, such as the heart wall, at different times is selected. For example, FIG. 4 shows a colored (Doppler tissue velocity) M-mode data corresponding to the curved line 38 tracking the heart wall throughout a sequence. Where the curved lines 38 have a thickness associated with multiple samples, the samples are averaged, selected or otherwise combined to provide data for each of a plurality of spatial locations along the curved line 38.

In act 32, rotation components of the heart are determined as a function of the ultrasound data. A processor determines the rotation components. The rotation components are circumferential or latitude displacements associated with short axis planes or motion. Rotation for short axis planes which are not orthogonal to the longitudinal axis may be used. Longitudinal, three-dimensional and/or other displacements may be determined. The displacements are determined using speckle or feature tracking from ultrasound data (e.g., B-mode data) representing the tissue at different times. The displacement as a function of time is a tissue velocity. In alternative embodiments, Doppler velocity information, with angle correction, is used to determine the rotation component. Other rotation components may be used, such as timing or amount of rotation relative to the heart cycle.

The rotation components are calculated from ultrasound data for different locations, the different times or both the different locations and different times. For example, rotations are calculated from ultrasound data representing different spatial locations in a same frame of data, different scan planes, and/or different times. Different locations include locations at different portions or spaced along a substantially longitudinal axis of the heart. The locations are at tissue spaced from the axis, but have different longitudinal positions. The longitudinal axis generally extends from the base to the apex of the left ventricle. Rotations at different longitudinal locations provide relative twist information. In one embodiment, rotations at the apex, at the base, and at one or more mid-levels along the longitudinal axis are determined.

Figure 11:
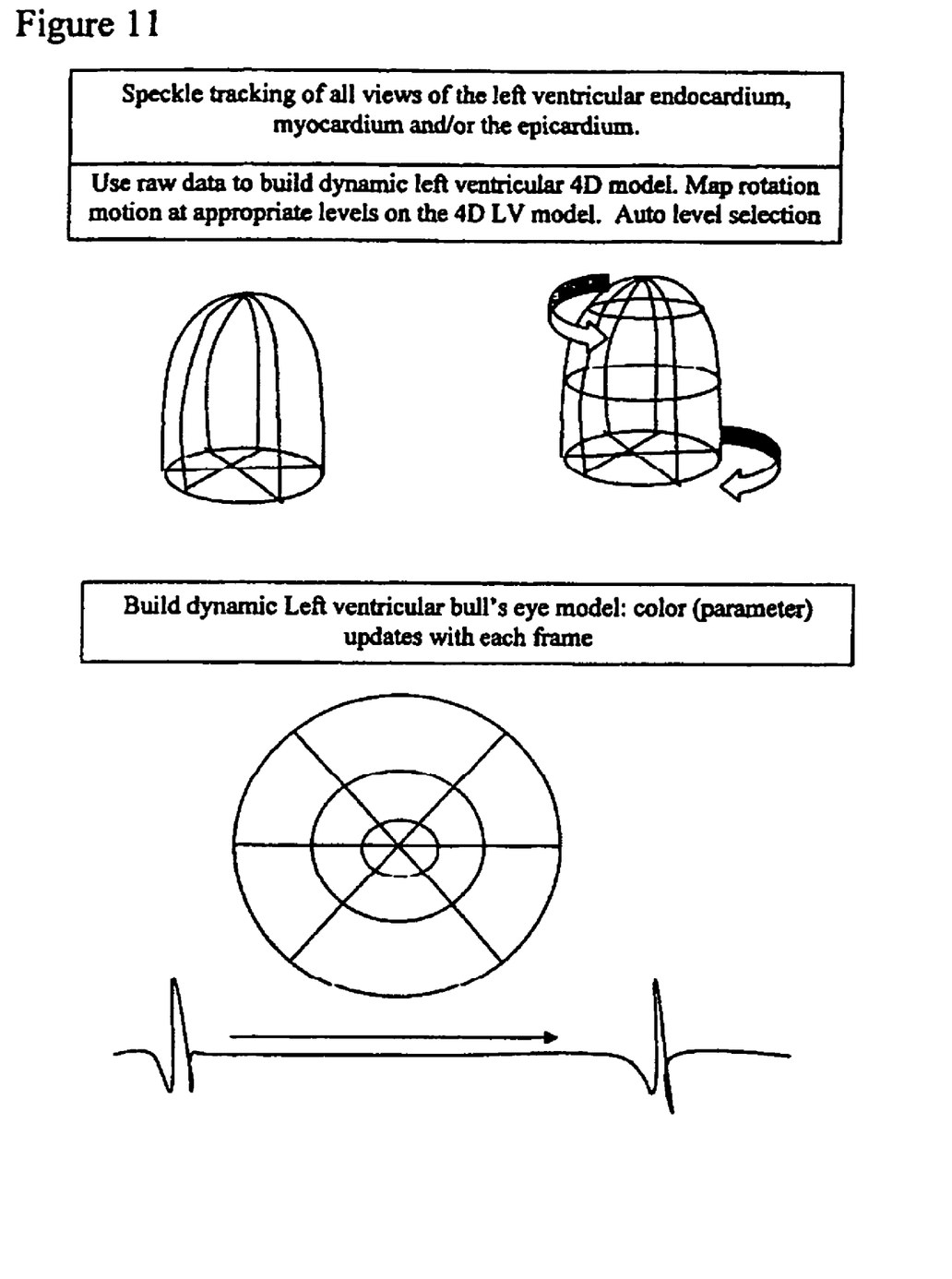
FIG. 11 is a graphical representation and flow chart for generating a display of rotation information in one embodiment.

FIG. 11 shows speckle tracking to determine rotation. For example, speckle tracking is performed for all views of the left ventricular endocardium, myocardium and/or epicardium.

Values of the rotation components may be calculated for each of the curved lines 38. For example, B-mode ultrasound data is used to calculate the rotation component for each spatial location or segment along the sequence of longitudinal, latitudinal and/or other curved lines 38. The rotation component represents rotation for a portion of the heart tissue in this example. In particular, the rotation for the heart wall, such as circumferential displacement, is calculated for the heart wall locations throughout a sequence.

The rotation components are mapped to display values. For example, rotation components are mapped to color (e.g., RGB) or gray scale values. Rotation in different directions may be mapped with different colors, such as one color being used for clockwise and a different color being used for counterclockwise rotation. One or more maps or mapping functions may be available. Depending on the application or user selection, a map is selected for mapping the rotation components or a sequence. The rotation components modulate the display values. For example, the display value is selected as a function of the identification of relative phasing of rotation components of a spatial location on the heart wall relative to the heart cycle.

Combinations of data may be mapped. For example, the combination of rotation and an amount of perfusion or contrast agent information are linearly or non-linearly combined and mapped to the three-dimensional representation. Another combination is of rotations, such as a gradient of rotation. More than one rotation are combined or compared to determine a gradient. In one example, the rotations for the epicardium and endocardium are determined separately. The gradient between the tissue layers is calculated and mapped to the surface 42.

FIG. 11 shows building the dynamic left ventricular model. The rotation motion is mapped at appropriate levels or longitudinal locations on the model. The model of FIG. 11 is a beutel or wire frame with three short axis views. The rotation is shown by arrows, but color or other mapping may be used. More than two levels of arrows may be automatically selected and displayed.

In act 34, a three-dimensional representation is displayed as a function of the rotation components. The three-dimensional representation represents at least a portion of the heart as an image. The image represents the rotation components at a particular time.

The shape of the portion or apparent shape of the three-dimensional representation may be derived from the ultrasound data. For example, a parametric surface is formed as a function of the curved lines 38. The assumed, set or tracked relative position of the curved lines is used to form the contour of the parametric surface. For example, FIG. 5 shows a surface 42 of at least a portion of the heart corresponding to the curved lines 38. The relative position of the curved lines 38 from different views at a same or similar time provides the framework or contour of the image. Both the endocardial and epicardial surfaces may be tracked and used to display a common or adjacent parametric surface, showing relative twist, mass, shear strain or other characteristics. As another example, the relative position of the curved lines 38 defines the relative locations of data within a two dimensional polar plot 44 shown in FIG. 6. Alternatively, a set or modeled shape is used with or without derivation from the ultrasound data.

The rotation components are mapped to the three-dimensional representation in one embodiment. For example, a surface is modulated as a function of the rotation components. Different locations on the surface appear differently (color, shade, brightness, texture or other differentiator) based on different rotation component values. Alternatively, the shape or contour of the three-dimensional representation distorts as a function of the rotation components.

For spatial locations on the surface 42, the polar plot 44, graph or other three-dimensional representation not at a curved line 38, data is interpolated from the motion parameters for the nearest curved lines. Display values may alternatively be interpolated. The closeness of the curved line provides a relative weighting of the contribution of data from different curved lines. Spherical or other interpolation is used. Alternatively, a nearest neighbor selection is used. The interpolated or other data for the parametric surface is or is not spatially filtered. Where ultrasound data is available to other locations, the interpolation may be avoided.

FIG. 11 shows building the polar plot from the wire frame. Color or other display indicia indicate rotation for different segments represented on the polar plot. The indicia are updated or mapped for each frame in a sequence. The sequence extends over a portion of or one or more heart cycles.

The three dimensional representation is formed for each temporal position in a sequence. By repeating the determination of rotation components and generation of three-dimensional representations as a function of time, the sequence results. The sequence is a video clip which runs through at least a portion of the heart cycle. By displaying the sequence or a portion of the sequence, the parametric surface is dynamically displayed. For example, a video clip of the parametric surface representing a portion of the heart is displayed. By displaying the dynamic parametric surface in synchronization with the heart cycle, the user may more likely understand or be able to diagnose heart motion abnormalities or heart disease.

A processor may calculate other values, such as twist, torsion or twist and torsion. Twist and torsion are calculated as a function of rotation components. Differences in circumferential displacement indicate an amount of twist. For example, the difference in magnitude of rotation of the apex relative to the base indicates twist. The apical and basal rotations may be values for particular locations or may be means. The twist divided by the longitudinal length indicates torsion. The longitudinal length of the heart is determined from the contour lines as the distance from the apex to the base.

The calculations are repeated for different times within a heart cycle. The rotation components and/or longitudinal length may vary throughout the cycle, so twist and/or torsion may vary as a function of time. Twist and/or torsion for the entire heart cycle may be determined. The rotation components, longitudinal lengths, twist or torsion throughout the heart cycle are averaged. Alternatively, a peak, minimum or median value is determined.

Figure 12:
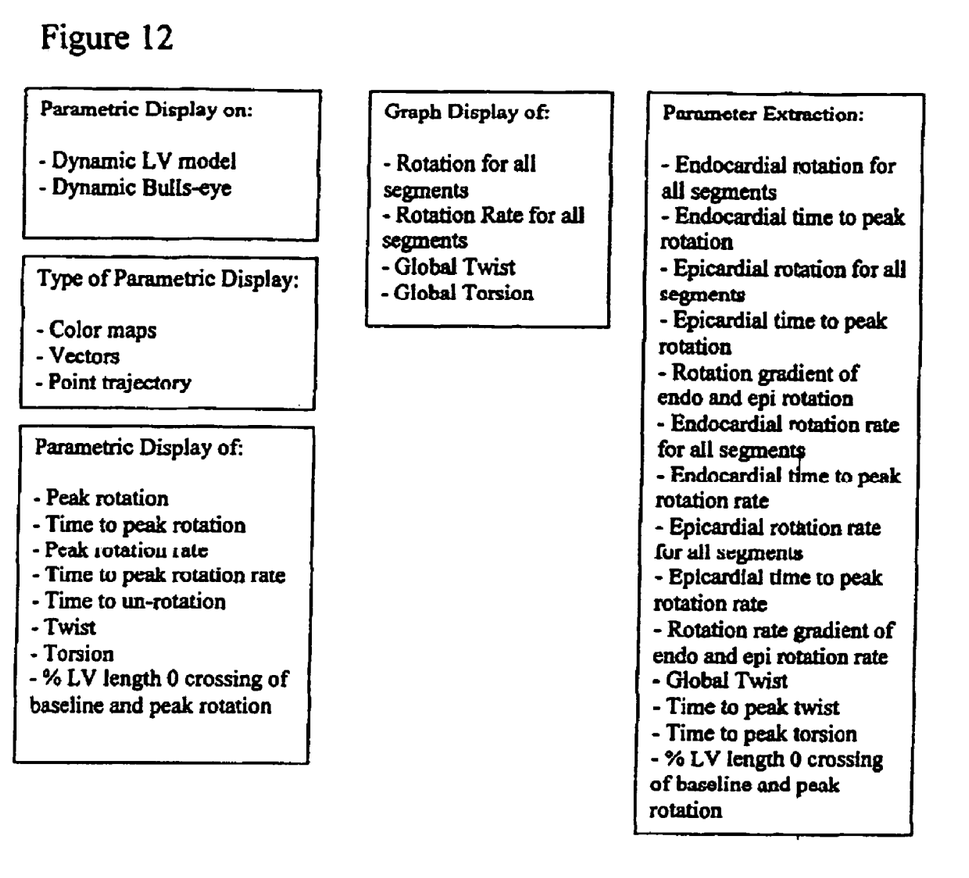
FIG. 12 is a graphical representation of output data options in one embodiment.

FIG. 12 shows various output options useable individually or in combinations. Different types of parametric displays, parameter to be mapped and/or structure which rotation is mapped to may be used. Graphs may be displayed. Various parameters may be extracted for mapping or output of the value.

Ultrasound data representing a volume may be acquired. The three-dimensional data set is formatted to a three-dimensional grid, in a polar coordinate format or combinations thereof (e.g., multiple scan converted planes arranged relative to each other in a polar coordinate format). The desired views may be extracted from the data. For example, tissue locations are identified, such as the longitudinal axis, an apical segment, apex, mitral valve, basal segment, mid segment, papillary level and/or other locations. Cut-planes through the volume intersecting the desired tissue locations are defined, such as cut-planes orthogonal to the longitudinal axis in a multi-planar reconstruction. The rotational components, such as the circumferential displacement, three-dimensional representations and/or calculations are then determined as discussed above from ultrasound data extracted from the volume data set at the cut-planes. Where data representing the volume at different times is available, the tissue locations may be tracked so that the cut-planes shift with the tissue locations as a function of time.

Instructions for implementing the methods for representing rotation of a heart with ultrasound are provided on computer-readable storage media or memories, such as a cache, buffer, RAM, removable media, hard drive, the memory 22 or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer or system.

The instructions cause the processor to determine rotation, twist, torsion or combinations thereof of the heart from ultrasound data. A three-dimensional representation of the rotation, twist, torsion or combinations thereof is displayed.

By displaying a twist component along the longitudinal extension of the ventricle, the overall rotation, twist and torsion may be used for diagnosis. Displaying the three-dimensional representation assists the user in visualizing the amount of rotation or twist. Three-dimensional rotation may be determined without a volume scan from long and short axis views. Alternatively, volume scanning may assure that the short axis information remains at the same tissue by tracking the tissue and repositioning the short axis multiplanar reconstructions for more accurate calculation of twist and torsion.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for representing rotation of a heart with ultrasound, the method comprising:

acquiring ultrasound data, with an ultrasound system, representing the heart along at least two different short axis planes, the ultrasound data representing the heart at different times;

determining, from ultrasound data, first and second rotation components of the heart as circumferential displacements associated with the different short axis planes at first and second different longitudinal locations, respectively, of the heart, the at least first and second short axis planes corresponding to the first and second longitudinal locations, respectively, the first longitudinal location and corresponding short axis plane offset longitudinally from the second longitudinal location and corresponding short axis plane; and generating a three-dimensional representation of the heart, the three-dimensional representation having a surface with values modulated by the first and second rotation components at different locations on the surface;

wherein determining comprises determining, as a function of the ultrasound data, the first and second rotation components of the heart, the first longitudinal location being along a different portion of a longitudinal axis of the heart than the second longitudinal location.

2. The method of claim 1 wherein acquiring the ultrasound data comprises:

acquiring the ultrasound data from apical four chamber, apical two chamber and apical long axis views at different times in at least a portion of a heart cycle; and identifying the ultrasound data associated with heart tissue from each of the views;

wherein determining comprises determining the first and second rotation components as a function of speckle or feature tracking of the heart tissue within at least two of the views.

3. The method of claim 1 wherein acquiring comprises acquiring as a function of a volume scan.

4. The method of claim 1 wherein determining comprises determining the first and second rotation components as first and second tissue velocities.

5. The method of claim 1 wherein generating comprises displaying the three-dimensional representation as part of a video clip running through at least a portion of a heart cycle.

6. The method of claim 1 wherein generating comprises displaying the three dimensional representation as at least a portion of the heart.

7. The method of claim 6 further comprising:

determining a shape of the portion from the ultrasound data;

wherein displaying comprises mapping the first and second rotation components on the shape, distorting the shape as a function of the rotation components, or combinations thereof.

8. The method of claim 1 further comprising:

repeating the determining and generating as a function of time, the generating providing a sequence of the three-dimensional representations dynamically mapped with rotation components as a function of time.

9. The method of claim 1 further comprising:

calculating a twist, torsion or twist and torsion as a function of the first and second rotation components.

10. The method of claim 1 wherein determining comprises determining the first and second rotation components as an amount of rotation relative to a heart cycle.

* * * * *